(12) United States Patent
Threewitt et al.

(10) Patent No.: US 7,968,498 B2
(45) Date of Patent: Jun. 28, 2011

(54) WEED CONTROL PROCESS COMPRISING THE APPLICATION OF MESOTRIONE AND SECOND HERBICIDE

(75) Inventors: Thomas Buntin Threewitt, Greensboro, NC (US); Dennis Eugene Stamm, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 655 days.

(21) Appl. No.: 10/520,367

(22) PCT Filed: Jun. 10, 2003

(86) PCT No.: PCT/IB03/03132
§ 371 (c)(1),
(2), (4) Date: Jan. 6, 2005

(87) PCT Pub. No.: WO2004/004459
PCT Pub. Date: Jan. 15, 2004

(65) Prior Publication Data
US 2006/0196115 A1    Sep. 7, 2006

(30) Foreign Application Priority Data

Jul. 4, 2002 (GB) .................................. 0215544.8

(51) Int. Cl.
*A01N 63/00* (2006.01)
(52) U.S. Cl. ........................................ 504/118; 514/129
(58) Field of Classification Search .................. 504/130, 504/133, 134, 136, 144, 145; 514/118
See application file for complete search history.

(56) References Cited

U.S. PATENT DOCUMENTS 6,723,681 B2 * 4/2004 Hacker et al. ................. 504/127

FOREIGN PATENT DOCUMENTS

| WO | WO 9105469 A | 5/1991 |
| WO | WO 9748276 | 12/1997 |
| WO | WO 0003592 | 1/2000 |
| WO | WO 0217719 | 3/2002 |
| WO | WO 02100173 | 12/2002 |

OTHER PUBLICATIONS

N.L. Kent, A.D. Evers; technology of Cereals An Introduction for Students of Food Science and Agriculture; 1994; Elsevier Science Ltd.; Fourth Edition; p. 1.*
Derek Comes; Synergistic Herbicidal Compostions Comprising Mesotrione; Dec. 19, 2002; International Application Published under the PCT;WO 02/100173.*
N.L. Kent, A.D. Evers; Technology of Cereals An Introduction for Students of Food Science and Agriculture; 1994; Elsevier Science Ltd.; Fourth Edition; p. 1.*

* cited by examiner

*Primary Examiner* — Karlheinz R Skowronek
*Assistant Examiner* — Ali Soroush
(74) *Attorney, Agent, or Firm* — William A. Teoli, Jr.

(57) ABSTRACT

A novel process for controlling weeds in a crop comprising *sorghum*, the process comprising the application of a herbicidally effective amount of: (i) mesotrione, and (ii) a second herbicide selected from one or more of prosulfuron, dicamba, 2,4-D, halosulfuron-methyl and quinclorac to the locus of the weeds is disclosed.

8 Claims, No Drawings

WEED CONTROL PROCESS COMPRISING THE APPLICATION OF MESOTRIONE AND SECOND HERBICIDE

The present invention relates to a process for controlling unwanted vegetation in a crop comprising *sorghum*, using a mixture of mesotrione and another herbicide.

The protection of crops from weeds and other vegetation that inhibits crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Commercial herbicides and some that are still in development are described in The Pesticide Manual, 12th edition, published in 2000 by the British Crop Protection Council. All the herbicides specifically named in this application can be found in The Pesticides Manual.

Many herbicides also damage crop plants. The control of weeds in a growing crop therefore requires the use of so-called 'selective' herbicides which are chosen to kill the weeds while leaving the crop undamaged. Few selective herbicides are selective enough to kill all the weeds and leave the crop completely untouched. In practice, the use of most selective herbicides is actually a balance between applying enough herbicide to acceptably control most of the weeds whilst causing only minimal crop damage.

One known selective herbicide is mesotrione, chemical name 2-(2-nitro-4-sulfonylbenzoyl)-cyclohexane dione. This is known largely for use to control weeds in a corn crop, both before the crop emerges from the ground (pre-emergent) and after (post-emergent).

*Sorghum* (*Sorghum bicolour*) is another commercially important crop. Mesotrione can be used pre-emergent and post-emergent over *sorghum* crops, but its post-emergent use is limited by the damage caused to the *sorghum* at mesotrione application rates that effectively control weeds.

We have discovered that by adding certain other herbicides to mesotrione, not only is the level of damage to weeds increased (as might be expected), but also, unexpectedly, the damage to the *sorghum* crop is reduced. The reduction of crop damage in this way is often referred to as 'safening'. This surprising safening effect enables mesotrione to be used over *sorghum* at herbicidally effective rates while causing little or no crop damage. This is an important practical extension to the scope of use of an existing herbicide.

According to the present invention there is provided a process for controlling weeds in a crop comprising *sorghum*, the process comprising the application of a herbicidally effective amount of;
i) mesotrione, and
ii) a second herbicide selected from one or more of prosulfuron, dicamba, 2,4-D, halosulfuron-methyl and quinclorac.

The mesotrione and second herbicide may be applied sequentially or at the same time. If applied at the same time, this may be as separate compositions or as a single composition.

The use of one or more of prosulfuron, dicamba, 2,4-D, halosulfuron-methyl and quinclorac to safen mesotrione, when applied over *sorghum* is novel and the effect is surprising.

The amount of mesotrione used in the process is generally between 50 and 300 g/ha, preferably between 70 and 200 g/ha and most preferably between 80 and 150 g/ha.

The process generally uses 0.5% to 400%, preferably 5 to 350% by weight of the second herbicide based on the concentration of mesotrione. Prosulfuron and halosulfuron-methyl are more preferably used at an amount between 5 and 100% based on the weight of mesotrione, most preferably between 10 and 60%. Dicamba and 2,4-D are most preferably used at an amount between 100 and 300% based on the weight of mesotrione. The mesotrione and the second herbicide can be applied separately, in any order, or are applied together, but are preferably applied together as a mixture.

Weeds means any unwanted plant that is not *sorghum*, including grasses such as crabgrass (*Digitaria sanguinalis* L.) and broadleaf weeds such as velvetleaf (*Abutilon theophrasti* MEDIK). The process also works particularly well in controlling Kochia (Kochia).

Controlling means killing, damaging, or inhibiting the growth of the weed.

The process of the invention involves applying the composition by a convenient method to the locus of the weeds where control is desired. The "locus" is intended to include soil, seeds, and seedlings, as well as established vegetation. The benefit of the invention is seen most on post-emergent application, but pre-emergent application is also possible.

The herbicides used in the process of the present invention are suitably applied in the form of a herbicidal formulation, which preferably comprises an agriculturally acceptable carrier therefore. In practice, the herbicides are applied as one or more formulations containing the various adjuvants and carriers known to or used in the industry for facilitating application and efficacy. The choice of formulation and mode of application for any given compound may affect its activity, and selection will be made accordingly. The herbicides used in the invention may thus be formulated as granules, as wettable powders, as emulsifiable concentrates, as powders or dusts, as flowables, as solutions, as suspensions or emulsions, or as controlled release forms such as microcapsules. These formulations may contain as little as about 0.5% to as much as about 95% or more by weight of active ingredient. The optimum amount for any given compound will depend upon formulation, application equipment, and nature of the plants to be controlled.

Wettable powders are in the form of finely divided particles that disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Suspension concentrates are high concentration suspensions of solid herbicide in water.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids that act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples are alkyl and alkylaryl sulphonates and sulphates and their salts; polyhydric alcohols; polyethoxylated alcohols; esters and fatty amines. These agents, when used, normally comprise from 0.1% to 15% by weight of the formulation.

Another suitable additive is crop oil concentrate (COC) which is well known for herbicides and is a mixtures of petroleum oils and non-ionic surfactants, available as, for example AGRI-DEX, PENETRATOR, and PENETRATOR PLUS all from Helena Chemical Company, HERBIMAX from UAP, ES CROP OIL PLUS from Gromark, and CROP OIL PLUS, from Wilfarm, (83% parafinic oil, 17% emulsifier surfactant). Other possible additives include urea ammonium nitrate, a fertiliser, methylated seed oil and ammonium sulphate.

Each of the above formulations can be prepared as a package containing the herbicide together with other ingredients of the formulation (diluents, emulsifiers, surfactants, etc.), the selection and use of which will be known to those skilled in the art. The formulations can also be prepared by a tank mix method, in which the ingredients are obtained separately and combined at the grower site.

A commercial formulation of mesotrione is available under the trade mark 'Callisto' from Syngenta AG. Callisto is a suspension concentrate of mesotrione.

A commercial formulation of prosulfuron is available under the trade mark 'Peak 57 WG' from Syngenta AG, which is in the form of a wettable granule, added to water just before application.

A commercial formulation of dicamba is available under the trademark 'Banvel' from Syngenta AG.

2,4-D is widely commercially available as a number of different salts, including dimethylammonium, diethanolammonium, triethanolammonium and sodium. The butyl ester, ioooctyl ester and dimethylammonium salts are preferred.

A commercial formulation of halosulfuron-methyl is available under the trademark 'Permit 75 WG' from Monsanto, which is in the form of a wettable granule, added to water just before application.

A commercial formulation of quinclorac is available under the trademark 'Paramount 75 WG' from BASF, which is in the form of a wettable granule, added to water just before application.

These formulations can be applied to the locus of the weeds by conventional methods. Dust and liquid compositions, for example, can be applied by the use of power-dusters, broom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as disking, dragging or mixing operations.

The following examples illustrate the invention, but are not to be regarded as limiting.

EXAMPLES

Various herbicidal compositions were applied to test plots comprising *sorghum* and test weeds (primarily crabgrass and several pigweed spp.). The herbicidal compositions are specified in Table 1 below. Essentially, these comprised, as active herbicidal components, mesotrione both alone and in combination with prosulfuron, dicamba, 2,4-D, halosulfuron-methyl and quinclorac, in the form of commercially available formulations.

TABLE 1

| Active Ingredient | Composition | | | | | | |
|---|---|---|---|---|---|---|---|
|  | 1 | 2 | 3 | 4 | 5 | 6 | 7 |
| Callisto 4 SC | 105.0 | 105.0 | 105.0 | 105.0 | 105.0 | 105.0 | 105.0 |
| COC | 1.0 | 1.0 | 1.0 | 1.0 | 1.0 | 1.0 | 1.0 |
| 2.5 | 2.5 | 2.5 | 2.5 | 2.5 | 2.5 | 2.5 | 2.5 |
| Peak 57 WG | — | 20.0 | 40.0 | — | — | — | — |
| Banvel | — | — | — | 280.0 | — | — | — |
| 2,4-D amine 4 | — | — | — | — | 280.0 | — | — |
| Permit 75 WG | — | — | — | — | — | 36.0 | — |
| Paramount 75 WG | — | — | — | — | — | — | 280 |

In Table 1:

The amounts of herbicide are quoted as a rate equivalent to grams per hectare. The amounts of COC and UAN are quoted in % vol/vol of composition.

Callisto 4 SC is an aqueous mesotrione suspension concentrate, containing 400 g/l mesotrione, available from Syngenta.

COC is Crop Oil Concentrate available as Agridex.

UAN is urea ammonium nitrate, a fertiliser available in bulk.

Peak 57 WG is a prosulfuron composition comprising 57% of prosulfuron, available from Syngenta.

Banvel is a dicamba formulation containing 480 g/l of dicamba, from BASF.

2,4-D amine 4 is a formulation of the dimethylamine salt of 2,4-D containing 4 lb/gal of 2,4-D, sold under the name Weedar 64 available from Aventis.

Permit 75 WG is a granular formulation of halosulfuron methyl, containing 75% halosulfuron methyl from Monsanto.

Paramount 75WG is a granular formulation of quinclorac, containing 75% quinclorac from BASF.

The compositions were made by mixing the components together by shaking the spray containers (soda bottles) before application.

These compositions were applied at the rates (i.e. the amounts per hectare) indicated in Table 1 and the damage to both the *sorghum* and the weeds were noted seven days after application. The results are given in Table 2:

TABLE 2

| Composition | Crop (sorghum) damage (%) | Weed Damage (%) | |
|---|---|---|---|
| | | Weed 1 | Weed 2 |
| 1 | 13.0 | 40 | 40 |
| 2 | 3.7 | 50 | 50 |
| 3 | 3.0 | 56.7 | 56.7 |
| 4 | 5.0 | 43.3 | 43.3 |
| 5 | 0.7 | 53.3 | 53.3 |
| 6 | 5.0 | 50.0 | 50.0 |
| 7 | 6.7 | 33.3 | 33.3 |

The damage was rated visually, and is expressed as a percentage.

It can clearly be seen from the table that the additional use of one of the specified herbicides, not only increases weed damage, but also reduces crop injury. This is a totally unexpected effect.

The invention claimed is:

1. A process for controlling weeds in a *sorghum* crop while reducing injury to such crop caused by the post-emergent application of a herbicidally effective amount of mesotrione over such crop, the process comprising applying to the locus of the weeds a herbicidally effective amount of:
   (i) mesotrione, and
   (ii) a second herbicide selected from prosulfuron
wherein the mesotrione is applied post-emergent over such *sorghum* crop.

2. A process according to claim 1 in which the mesotrione is applied at a rate of between 50 and 300 g/ha.

3. A process according to claim 1 using 0.5 to 400% of the second herbicide, based on the concentration of mesotrione.

4. A process according to claim 1 in which mesotrione and the second herbicide are applied at the same time.

5. A process according to claim 1 in which mesotrione and the second herbicide are applied sequentially.

6. A process according to claim 1 in which mesotrione and the second herbicide are applied as separate compositions.

7. A process according to claim 1 in which mesotrione and the second herbicide are applied as a single composition.

8. A process according to claim 1 in which mesotrione and the second herbicide are applied post-emergent over such *sorghum* crop.

* * * * *